United States Patent
Watterson et al.

(10) Patent No.: US 7,097,588 B2
(45) Date of Patent: Aug. 29, 2006

(54) PROGRESIVE HEART RATE MONITOR DISPLAY (75) Inventors: Scott Watterson, Logan, UT (US); William T. Dalebout, N. Logan, UT (US); Kirk Lorrigan, Logan, UT (US); Darren Ashby, Richmond, UT (US)

(73) Assignee: Icon IP, Inc., Logan, UT (US)

( * ) Notice: Subject to any disclaimer, the term of this patent is extended or adjusted under 35 U.S.C. 154(b) by 456 days.

(21) Appl. No.: 10/367,117

(22) Filed: Feb. 14, 2003

(65) Prior Publication Data

US 2004/0162188 A1 Aug. 19, 2004

(51) Int. Cl.
*A63B 21/00* (2006.01)

(52) U.S. Cl. .................... 482/8; 482/1; 482/9; 482/900

(58) Field of Classification Search ............... 482/1–9, 482/51, 54, 900–902
See application file for complete search history.

(56) References Cited

U.S. PATENT DOCUMENTS

| | | | |
|---|---|---|---|
| 4,278,095 A | 7/1981 | Lapeyre | |
| 4,790,528 A | 12/1988 | Nakao et al. | |
| 4,842,266 A | 6/1989 | Sweeney, Sr. et al. | |
| 4,911,427 A | 3/1990 | Matsumoto et al. | |
| 4,998,725 A | 3/1991 | Watterson et al. | |
| 5,067,710 A * | 11/1991 | Watterson et al. | 482/3 |
| 5,104,120 A | 4/1992 | Watterson et al. | |
| 5,149,084 A | 9/1992 | Dalebout et al. | |
| 5,313,942 A | 5/1994 | Platzker | |
| 5,318,487 A * | 6/1994 | Golen et al. | 482/5 |
| 5,410,472 A | 4/1995 | Anderson | |
| 5,462,504 A | 10/1995 | Trulaske et al. | |
| 5,474,090 A | 12/1995 | Begun et al. | |
| 5,524,637 A * | 6/1996 | Erickson | 600/592 |
| 5,527,239 A * | 6/1996 | Abbondanza | 482/8 |
| 5,591,104 A | 1/1997 | Andrus et al. | |
| 5,769,755 A * | 6/1998 | Henry et al. | 482/8 |
| 5,888,172 A | 3/1999 | Andrus et al. | |
| 6,033,344 A | 3/2000 | Trulaske et al. | |
| 6,345,197 B1 * | 2/2002 | Fabrizio | 600/519 |
| 6,634,992 B1 | 10/2003 | Ogawa | |
| 6,648,798 B1 * | 11/2003 | Yoo | 482/8 |
| 6,783,482 B1 * | 8/2004 | Oglesby et al. | 482/54 |
| 6,798,378 B1 * | 9/2004 | Walters | 342/357.06 |
| 6,881,176 B1 * | 4/2005 | Oishi et al. | 482/8 |
| 6,902,513 B1 * | 6/2005 | McClure | 482/8 |

* cited by examiner

*Primary Examiner*—Glenn Richman
(74) *Attorney, Agent, or Firm*—Workman Nydegger (57) ABSTRACT

The present invention relates to heart rate monitor displays. More particularly, the present invention relates to methods and apparatuses for displaying a user's heart rate relative to a target heart rate. A progressive heart rate monitor display having two or more indicia adapted to indicate a users heart rate relative to a target heart rate and to signal changes in the user's heart rate is provided. The progressive heart rate monitor display can include a numeric display for representing the heart rate as a numeric value. A method of displaying a user's heart rate in which one or more of the indicia are actuated to signal changes in a user's heart rate relative to a target heart rate.

37 Claims, 4 Drawing Sheets

PROGRESIVE HEART RATE MONITOR DISPLAY

BACKGROUND OF THE INVENTION

1. The Field of the Invention

The present invention relates to heart rate monitor displays. More particularly, the present invention relates to methods and apparatuses for displaying a user's heart rate relative to a target heart rate.

2. The Relevant Technology

Heart rate monitor displays have been utilized in a variety of applications including, but not limited to, medical diagnostics, physical therapy, and long term care. More recently, heart rate monitor displays have been configured to be used with exercise equipment. Heart rate monitor displays allow an exerciser to determine his/her heart rate during exercise without needing to interrupt the exercise routine to manually detect his/her pulse. This allows the user to continue the exercise routine while providing indication of real time changes in the user's heart rate.

Existing heart rate monitor displays, while providing an improvement over a simple manual determination of heart rate, nevertheless suffer from several deficiencies. Often such displays depict the user's heart rate in a manner that is confusing or requires special training to decipher. Additionally, the displays can be difficult to read during an exercise routine or provide insufficient information to allow a user to tailor the exercise intensity to maximize the cardiovascular benefit of the exercise. Some displays fail to indicate a target heart rate or indicate needed changes to a user's exercising heart rate to attain the maximum exercise benefit. Where a target heart rate is provided, a visual relationship between the target heart rate and the user's heart rate is often difficult to determine.

BRIEF SUMMARY OF THE INVENTION

The present invention relates to heart rate monitor displays. More particularly, the present invention relates to methods and apparatuses for displaying a user's heart rate relative to a target heart rate. A progressive heart rate monitor display is provided for displaying a user's heart rate relative to a target heart rate. The progressive heart rate monitor display includes a plurality of indicia corresponding to different heart rates. Additionally, one or more of the indicia correspond to a target heart rate. The indicia are actuated to indicate a users heart rate and to signal changes in the user's heart rate. This permits the user to ascertain the relationship between the user's heart rate and the target heart rate.

According to one aspect of the present invention, the progressive heart rate monitor display includes a numeric display for representing the heart rate as a numeric value. This provides an additional indication of the user's heart rate that complements the visual indication provided by the indicia. According to another aspect of the present invention, a user interface is provided allowing the user to input information that can be used to automatically identify a target heart rate or select other parameters to be displayed.

A method of displaying a user's heart rate is also provided according to one aspect of the present invention. In the method, a plurality of indicia adapted to signal changes in a user's heart rate are provided. One or more of the indicia are identified as an indicator of a target heart rate. Once a target heart rate is selected, the user's heart rate is monitored. One or more of the indicia are actuated as an indication of the user's heart rate. In response to a change in the user's heart rate, a different one of the indicia is actuated.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
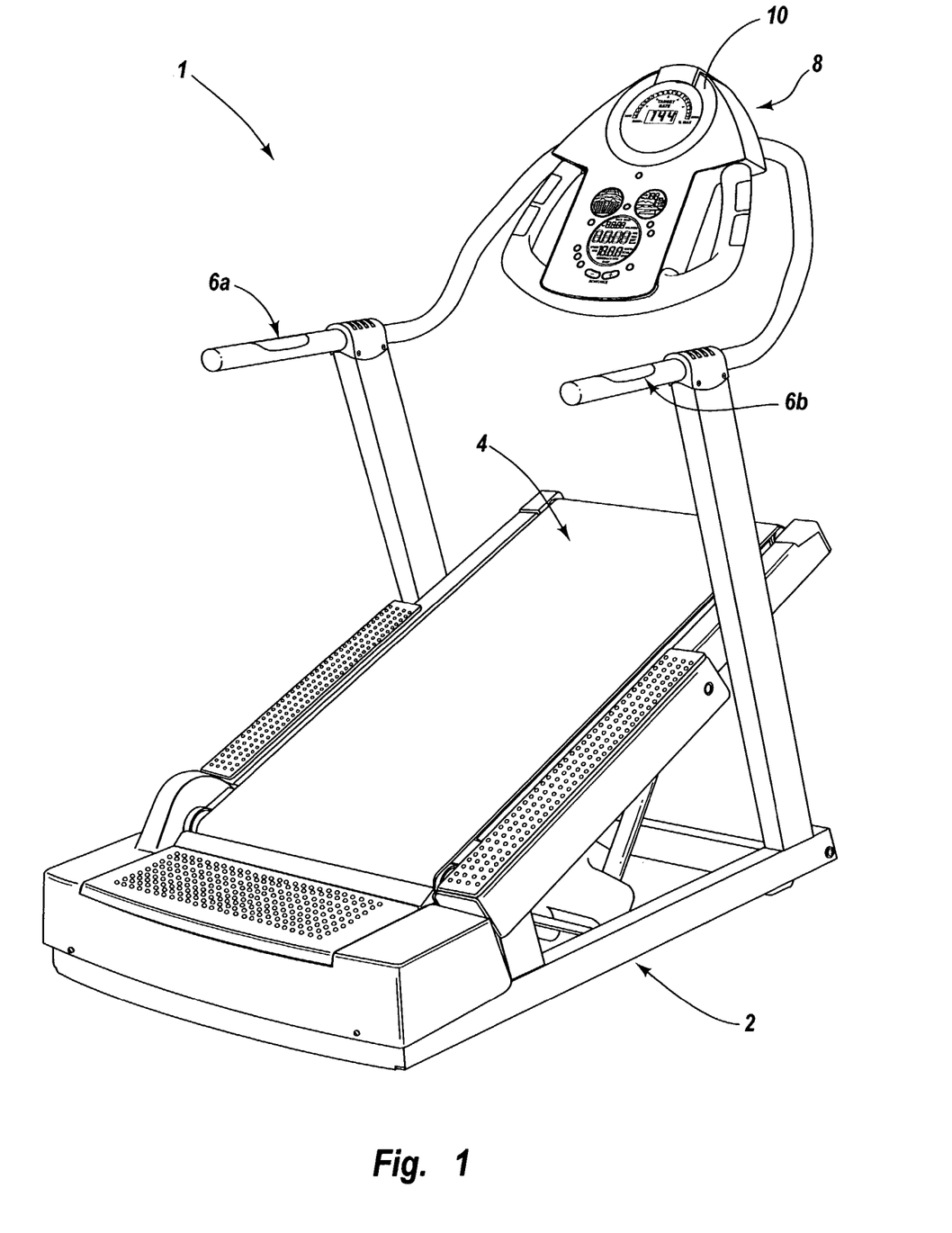
FIG. 1 illustrates an exercise apparatus having a progressive heart rate monitor display according to one aspect of the present invention.
Figure 2:
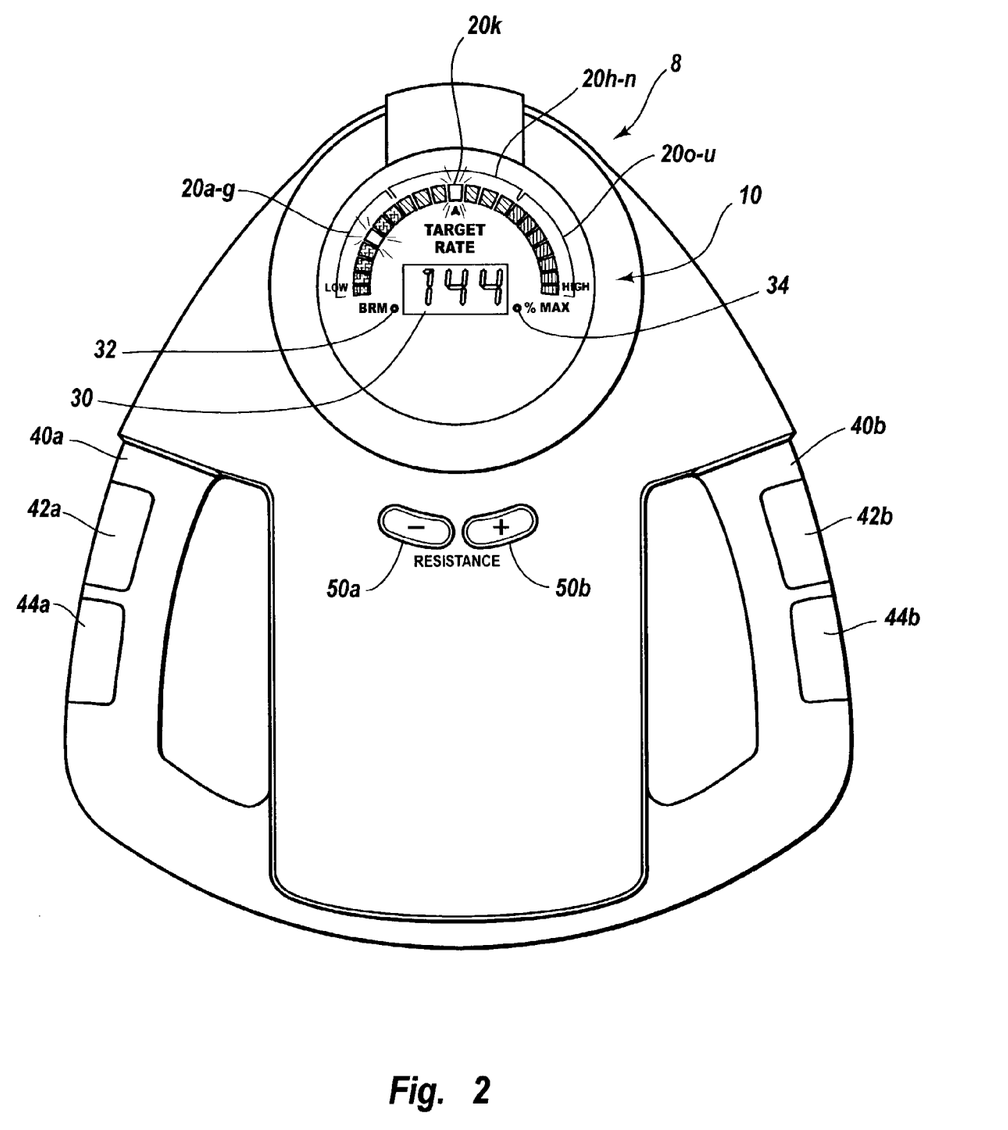
FIG. 2 shows a progressive heart rate monitor display according to one aspect of the present invention.
Figure 3:
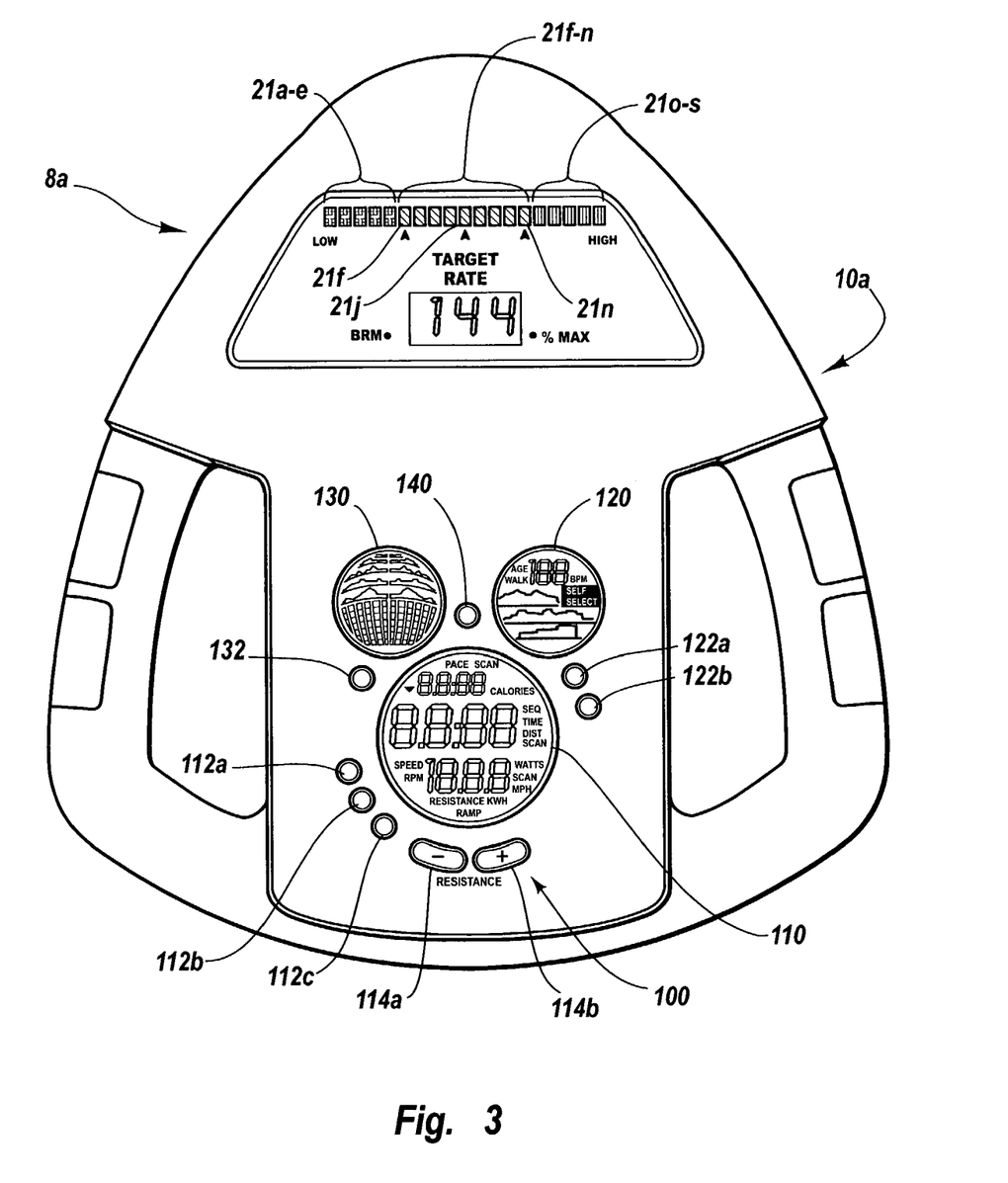
FIG. 3 illustrates the progressive heart rate display used in connection with a user interface according to one aspect of the present invention.
Figure 4:
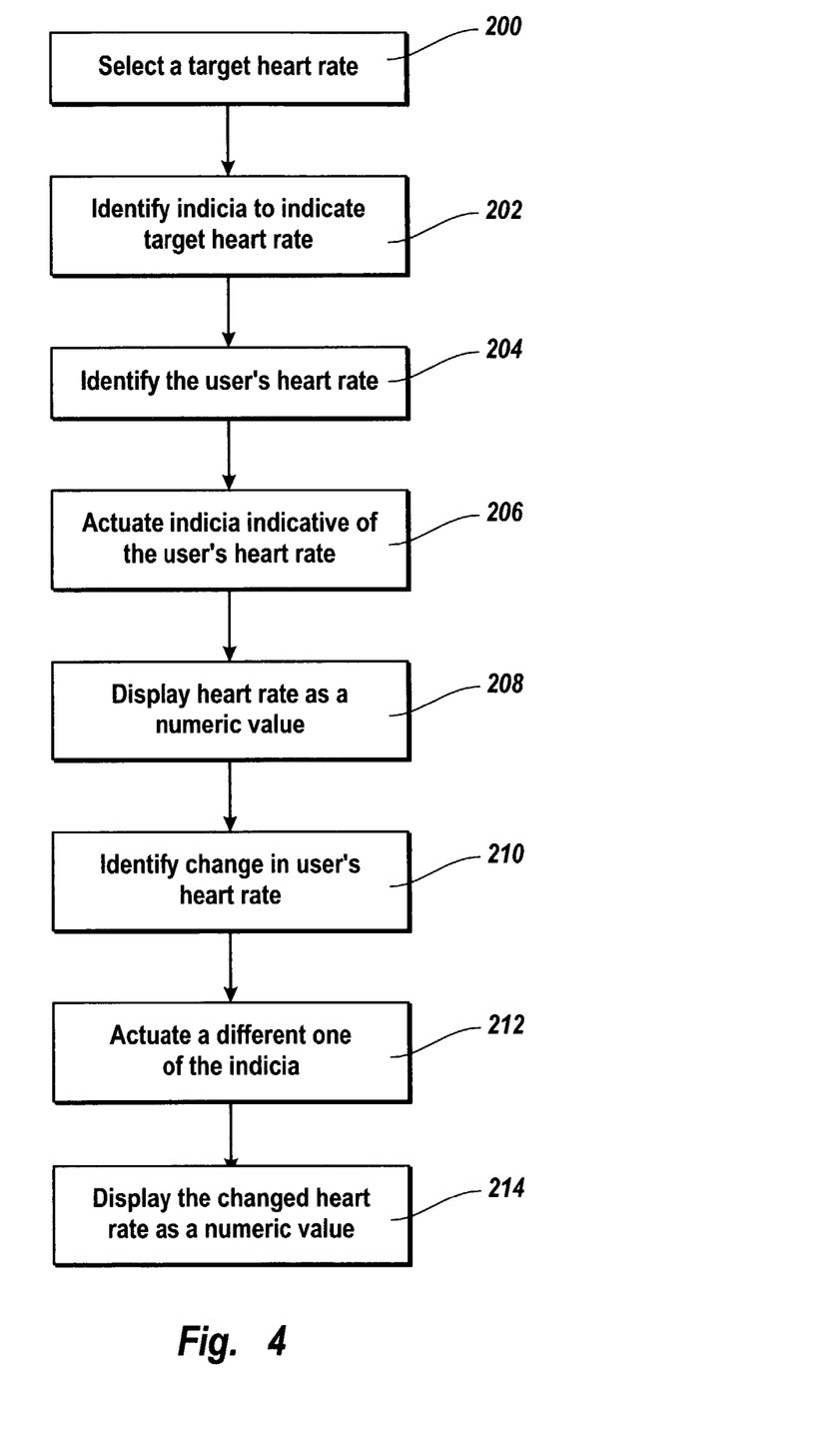
FIG. 4 is a flow diagram illustrating a method of displaying a user's heart rate according to one aspect of the present invention.

FIG. 1 shows an exercise apparatus 1 having a progressive heart rate monitor display 10 so as to depict an illustrative operating environment with which the progressive heart rate monitor display can be utilized according to one aspect of the present invention. FIG. 2 shows the progressive heart rate monitor display 10 in greater detail illustrating one manner in which display 10 can be utilized to depict a user's heart rate relative to a target heart rate according to one aspect of the present invention. FIG. 3 illustrates progressive heart rate display 10 depicting a user interface 100. FIG. 4 is a flow diagram illustrating a method of displaying a user's heart rate according to one aspect of the present invention.

With reference now to FIG. 1, there is shown a perspective view of an exercise apparatus 1 having a progressive heart rate monitor display 10 according to one aspect of the present invention. Exercise apparatus 1 is configured to permit a user to exercise in a home or commercial gym setting. The progressive heart rate monitor display 10 provides a mechanism for allowing the user to maximize the cardiovascular benefit of the exercise by identifying the user's heart rate relative to a desired target heart rate.

In the illustrated embodiment, exercise apparatus 1 comprises a treadmill apparatus adapted to allow a user to walk or run thereon. Exercise apparatus 1 comprises a frame 2, a treadbase 4, a handrail assembly 6a, b, a console 8, and a progressive heart rate monitor display 10. Frame 2 provides structural support to exercise apparatus 1. Treadbase 4 is coupled to frame 2 and provides a mechanism for allowing a user to exercise on exercise apparatus 1. In the illustrated embodiment, treadbase 4 is shown in an inclined position. Treadbase 4 is one example of a movable member.

Handrail assemblies 6a, b are coupled to frame 2. Handrail assemblies 6a, b enable a user to secure himself/herself during exercise. Console 8 is coupled to handrail assembly 6a, b in the illustrated configuration, however one skilled in the art may appreciate that the console may be coupled directly to the frame or be integrally coupled thereto. Console 8 provides an apparatus on which displays and user controls can be positioned. Progressive heart rate monitor display 10 is positioned on console 8. Progressive heart rate monitor display 10 provides a mechanism for allowing a user to maximize the cardiovascular benefit of the exercise by identifying the user's heart rate relative to a desired target heart rate. Progressive heart rate monitor display 10 will be discussed in greater detail with reference to FIGS. 2–4.

As will be appreciated by those skilled in the art, a variety of types and configurations of exercise apparatuses can be utilized without departing from the scope and spirit of the present invention. For example, in one embodiment the exercise apparatus comprises a stationary bicycle. In an alternative embodiment, the exercise apparatus comprises an elliptical trainer. In yet another embodiment, the exercise apparatus and the progressive heart rate monitor display comprise components of an exercise system.

With reference now to FIG. 2, there is shown a progressive heart rate monitor display 10 positioned on console 8 according to one aspect of the present invention. Progressive heart rate monitor display 10 displays the user's heart rate relative to a desired target heart rate. By displaying the user's heart rate relative to a target heart rate, progressive heart rate monitor display 10 permits a user to maximize the cardiovascular benefit of the exercise.

In the illustrated embodiment, progressive heart rate monitor display comprises indicia 20a–u and numeric display 30. Indicia 20a–u are configured to signal the status of a user's heart rate. Each of the indicia corresponds to a different heart rate. One of the indicia corresponds to a target heart rate. The target heart rate can be the heart rate that is the most efficient for fat burning, or cardiovascular fitness, for example. In the illustrated embodiment, indicia 20k corresponds to the target heart rate.

The term "user's heart rate" as referred to herein may refer to the user's actual heart rate, measured heart rate, estimated heart rate, indicated heart rate, averaged heart rate, or the like. The user's heart rate can be based on the method of detecting, measuring, displaying, and/or processing the heart rate. For example, the monitoring apparatus used to detect the user's actual heart rate and the heart rate monitor display can provide a substantially real-time indication of the user's actual heart rate. In another embodiment, the user's heart rate is an indication of the average heart rate over the preceding 30 seconds or a similar period of time.

The target heart rate can be provided utilizing a variety of mechanisms or methods. For example, the target heart rate can be a heart rate selected by the user. Alternatively, the target heart rate can be automatically selected. In one embodiment, the target heart rate is computed utilizing standard charts. In an alternative embodiment, the target heart rate is selected at least in part based on the physiological characteristics of the user such as age, weight, height, body mass index, or the like.

At least one of indicia 20a–u are actuated as an indication of the user's heart rate. In one embodiment, all the indicia leading up to the indicia corresponding to the user's heart rate are actuated. In another embodiment, only the indicia corresponding to the user's heart rate is actuated. Actuation of the indicia is dependent on the type and configuration of indicia utilized. In one embodiment, the indicia comprise light emitting diodes and are actuated by illuminating the diodes. In an alternative embodiment, the indicia comprise groupings of pixels on a liquid crystal display and actuation of the indicia comprises shading, lightening, or darkening the indicia.

Because indicia 20k corresponds to a target heart rate, actuation of an indicia provides another indication of the user's heart rate relative to a target heart rate. For example, indicia 20k is actuated when the user's heart rate corresponds to the target heart rate. One or more of the indicia above indicia 20k are actuated when the user's heart rate is above the target heart rate. One or more of the indicia below indicia 20k are actuated when the user's heart rate is below the target heart rate.

Indicia 20a–u provide a progressive display of potential heart rates. In the illustrated embodiment, each of the indicia corresponds to a heart rate having a specific range of beats per minute. For example, each indicia can correspond to a range of +/−2 beats per minute. In another embodiment, the range of beats per minute can be greater or lesser than +/−2 beats per minute. Also by way of example, indicia 20a can correspond to a range of 60–64 beats per minute while indicia 20u can correspond to a range of 144–148 beats per minute and indicia 20k corresponds to a target heart rate of 116–120 beats per minute. In other words, in the exemplary embodiment, each indicia provides an indication of a consistent range of beats per minute. Additionally, a single indicia e.g. 20k represents a single target heart rate. Other ranges of beats per minute associated with indicia 20a–20u can be possible that relate to the human spectrum.

A variety of types and configurations of indicia can be utilized to provide an indication of a user's heart rate relative to a target heart rate without departing from the scope and spirit of the present invention. For example, the indicia can be programmed to provide a dynamic indicator of a heart rate relative to a target heart rate. A variety of different types and configurations of mechanisms for providing a dynamic indicator can be utilized. For instance, in one embodiment the indicia are weighted such that indicia 20a, b and 20t, u represent a large range of beats per minute corresponding to high and low heart rates. When the heart rate approaches the target heart rate, the range of beats per minute represented by each indicia is substantially narrowed to provide a more detailed view of the user's actual heart rate.

In an alternative embodiment, a variety of indicia can be utilized to represent a target heart rate. In the embodiment, a single target heart rate is utilized. The indicia representing the target heart rate changes based on the user's actual heart rate relative to the target heart rate. When the user's heart rate is substantially below the target heart rate, the indicia that represents the target heart rate is one of the right most indicia, e.g. indicia 20q. When the user's heart rate is substantially above the target heart rate, the indicia that represents the target heart rate changes to one of the left most indicia, e.g. indicia 20e. When the user's heart rate approximates the target heart rate, one of the middle indicia can represent the target heart rate, e.g. indicia 20k.

Where more than one indicia can represent the target heart rate, an indicator is utilized to signal which of the indicia represents the target heart rate. For example, in one embodiment, the indicia representing the target heart rate is actuated. In this embodiment, the indicia representing the target heart rate is actuated in a manner so as to differentiate the target heart rate from the user's actual heart rate. For example, the user's heart rate can comprise a flashing indication while the target heart rate is a constant non-flashing indication. Alternatively, a different color or intensity of light can be utilized to differentiate the target heart rate from the user's actual heart rate. Alternatively, an arrow can be actuated or illuminated to indicate the target heart rate.

In the embodiment illustrated in FIG. 2, indicia 20a–u have different colors to indicate whether the user's heart rate is below, approximating, or above the target heart rate. For example, indicia 20a–g can have an amber color indicating a heart rate below the target heart rate. Indicia 20h–n can have a green color indicating a heart rate approximating the target hear rate. Indicia 20o–u can have a red color indicating a heart rate above the target heart rate. As will be appreciated by those skilled in the art, a variety of types and configurations of indicia, colors, patterns, and/or indications of target heart rate can be utilized without departing from the scope and spirit of the present invention. For example, in one embodiment the indicia comprise colored light emitting diodes or light bulbs. In another embodiment, different color intensities are utilized to indicate the relationship between the user's heart rate and the target heart rate.

Numeric display 30 is included as a component of progressive heart rate monitor display 10. In the illustrated embodiment, numeric display 30 is positioned adjacent indicia 20. Numeric display 30 is adapted to represent the user's heart rate as a numeric value. By displaying the user's heart rate as a numeric value, numeric display 30 complements the display of the user's heart rate relative to a target heart rate provided by indicia 20a–u. In one embodiment, numeric display 30 comprises a seven-segment display. In an alternative embodiment the numeric display comprises a liquid crystal display or light emitting diode display, or other display capable of presenting a visual representation of the numeric value of the user's heart rate.

In the illustrated embodiment, numeric display 30 is associated with a first indicator light 32 and a second indicator light 34. First and second indicator lights 32, 34 provide an indication of different parameters related to numeric display 30. For example, in the present embodiment, first indicator light 32 comprises a beats per minute indicator light while second indicator light 34 comprises a percentage of maximum safe heart rate indicator light. When first indicator light 32 is actuated, numeric display is displaying the user's heart rate in beats per minute. When the second indicator light 34 is actuated, the numeric display is indicating the percentage of the maximum recommended heart rate at which the user's heart is beating.

In the illustrated embodiment, there is also shown handgrip assemblies 40a, b and target heart rate selector buttons 50a, b. Handgrip assemblies 40a, b are coupled to console 8. Handgrip assemblies 40a, b are configured to provide a mechanism for monitoring the user's heart rate. Handgrip assemblies 40a, b include first electrodes 42a, b and second electrodes 44a, b. When gripped by a user, first electrodes 42a, b and second electrodes 44a, b utilize an electrical current to detect and monitor the user's heart rate. As will be appreciated by those skilled in the art, a variety of types and configurations of heart rate monitors can be utilized without departing from the scope and spirit of the present invention. For example, in one embodiment a continuous heart rate monitor is strapped directly to the user to provide hands-free monitoring the users heart rate. In another embodiment, a heart rate monitoring system having a heart rate monitor and progressive heart rate monitor display is provided.

Target heart rate selector buttons 50a, b provide an input mechanism allowing user to change one or more parameters related to the progressive heart rate monitor display. In one embodiment, target heart rate selector buttons 50a, b allow a user to select and/or change the target heart rate. In another embodiment, target heart rate selector buttons 50a, b provide a mechanism for inputting relevant physiological parameters and/or desired workout information such that the system can automatically select a target heart rate.

With reference now to FIG. 3, there is shown console 8a and progressive heart rate monitor display 10a according to another embodiment of the present invention. In the illustrated embodiment, a user interface 100 is positioned on console 8a in addition to progressive heart rate monitor display 10a. In the illustrated embodiment, progressive heart rate monitor display 10a includes indicia 21a–s. Indicia 21a–s are configured in a linear arrangement. Three different indicia 21f, j, n can be utilized as an indicator of a target heart rate. As will be appreciated by those skilled in the art, a variety of types and configurations of indicia can be utilized without departing from the scope and spirit of the present invention.

User interface 100 is coupled to console 8. User interface 100 provides a mechanism for displaying one or more parameters of the exercise apparatus to the user. Additionally, user interface 100 allows the user to input one or more items related to operation of the exercise apparatus. In the illustrated embodiment, user interface comprises a first display 110, a second display 120, a third display 130, and an enter button 140.

First display 110, second display 120, and third display 130 are adapted to display one or more parameters related to the exercise apparatus and/or user's workout to the user. In the illustrated embodiment, first display 110 displays information related to the exercise routine and data regarding the user. Examples of information related to the exercise routine may include, but are not limited to, speed, distance, incline, time, and rotations per minute. Examples of data regarding the user may include, but are not limited to, age, weight, calories burned, pace, biometrics, or other measurable characteristics or properties of the user.

Exercise apparatus control buttons 112a, b, c and resistance selector buttons 114a, b are also shown. Exercise apparatus control buttons 112a, b, c and resistance selector buttons 114a, b are associated with first display 110. Exercise apparatus control buttons 112a, b, c and resistance selector buttons 114a, b allow a user to input information related to the user, such as age, weight, height, and the like, while also controlling operation of the exercise apparatus. In one embodiment, the system utilizes information regarding the user to determine a target heart rate for use with progressive heart rate monitor display 10.

Second display 120 displays the target heart rate and provides tracking of the status of the selected workout routine. This allows the user to monitor his or her progress during a workout routine while monitoring the target heart rate. There is also shown heart rate selector control buttons 122a, b. Heart rate selector control buttons 122a, b allow the user to modify and/or change the target heart rate. Third display 130 displays information related to potential workout routines that can be selected by the user.

Third display 130 provides information including the duration and intensity of the workout routines. Program selector button 132 is also shown. Program selector button 132 is associated with third display 130. Program selector button 132 permits a user to select from among potential workout routines.

Enter button 140 allows a user to finalize a set of commands, or select a given set of display characteristics on one or more of displays 110, 120, 130. As will be appreciated by those skilled in the art, a variety of types and configurations of user interfaces can be utilized without departing from the scope and spirit of the present invention. For example, in one embodiment the user interface is integral with the progressive heart rate monitor display. In an alternative embodiment, the user interface includes a single display with a plurality of different screens between which the user can toggle.

As will be appreciated by those skilled in the art, a variety of types and configurations of progressive heart rate monitor displays can be utilized without departing from the scope and spirit of the present invention. For example, in one embodiment the progressive heart rate monitor display comprises a stand-alone feature that is not coupled to a console. In another embodiment, the progressive heart rate monitor display can be worn by the user during the workout. In yet another embodiment, the progressive heart rate monitor display is coupled to a console that is coupled to the frame of an exercise apparatus. In another embodiment, the progressive heart rate monitor display includes a number of input buttons configured to permit a user to input relevant physiological information. In yet another embodiment, the progressive heart rate monitor display comprises one of plurality of screens on a display between which a user can toggle. In yet another embodiment, the progressive heart rate monitor display comprises a plurality of indicia but does not include a numeric display. In still yet another embodiment, the progressive heart rate monitor display is configured to automatically change the intensity of the workout routine to assist the user in achieving the target heart rate. For example, the treadmill or other exercise device can include a feedback loop that identifies discrepancies between the user's heart rate and the target heart rate and adjusts the workout intensity such that the user's heart rate moves toward the target heart rate. In still yet another alternative embodiment, the progressive heart rate monitor display assists the user in selecting workout routines based on the physiological characteristics of the user.

With reference now to FIG. 4, there is shown a method of displaying a user's heart rate. In the method, a target heart rate is selected in step 200. Once the heart rate is selected an indicia is identified to indicate a target heart rate in step 202. Once the indicia corresponding to a target heart rate is identified, the user's heart rate is identified in step 204. The indicia indicative of the user's heart rate is then actuated in step 206. Once the indicia indicative of the user's heart rate is actuated, the user's heart rate can be displayed as a numeric value in step 208.

Optionally, changes in the user's heart rate are then identified in step 210. Once the changes in the user's heart rate have been identified, a different one of the indicia is actuated in step 212. Once a different one of the indicia has been actuated, the changed heart rate is displayed as a numeric value in step 214. Steps 210–214 can be repeated as often as is desirable to assist the user in approximating the desired heart rate during the course of the workout routine. Step 200–214 can be performed in any order that facilitates displaying the user's heart rate relative to a target heart rate. Additionally, one or more of steps 200–214 can be performed simultaneously. It will also be appreciated that one or more of steps 200–214 can be performed in a variety of manners and utilizing a variety of mechanisms. For example, the target heart rate can be selected by the user and input manually or automatically by the system utilizing physiological information related to the user.

A variety of types and configurations of methods for displaying a user's heart rate can be utilized without departing from the scope and spirit of the present invention. For example, in one embodiment, the user's heart rate is only displayed by the indicia and is not displayed as a numeric value. In another embodiment, the indicia indicative of the target heart rate is identified before the target heart rate is selected. In yet another embodiment, the target heart rate can either be selected by the user or be automatically selected based on physiological characteristics of the user or some other criteria.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An exercise system configured to display a user's heart rate relative to a target heart rate, the exercise system comprising:
   (i) an exercise apparatus comprising:
      a frame; and
      a movable member linked to the frame; and
   (ii) a progressive heart rate monitor display comprising a plurality of six or more non-numeric indicia which are arranged in a single array such that each of the non-numeric indicia are consecutively displayed, wherein at least one non-numeric indicia corresponding with the target heart rate is actuated and at least one indicia corresponding with the user's heart rate is actuated when the user's heart rate is not the same as the target heart rate to provide a visual non-numeric indication of the user's heart rate relative to a target heart rate.

2. The exercise system of claim 1, wherein the exercise system further comprises a numeric display for representing the heart rate as a numeric value.

3. The exercise system of claim 1, wherein the progressive heart rate monitor display provides a mechanism for allowing the user to maximize the cardiovascular benefit of the exercise by identifying the user's heart rate relative to a desired target heart rate.

4. The exercise system of claim 3, wherein the system can identify discrepancies between the user's heart rate and the target heart rate.

5. The exercise system of claim 4, wherein the system utilizes discrepancies between the user's heart rate and the target heart rate to adjust the intensity of the workout such that the user's heart rate moves toward the target heart rate.

6. The exercise system of claim 1, wherein the indicia are configured to signal changes in a user's heart rate.

7. The exercise system of claim 1, wherein the indicia provide a progressive display of potential heart rates.

8. The exercise system of claim 7, wherein each of the indicia corresponds to a heart rate having a specific range of beats per minute.

9. The exercise system of claim 1, wherein the indicia are weighted such that as the user's heart rate approaches the target heart rate a more detailed view of the user's actual heart rate is provided by the indicia than when the user's heart rate does not approximate the target heart rate.

10. The exercise system of claim 1, further comprising a user interface for inputting data.

11. The exercise system of claim 10, wherein the user interface permits the user to select a target heart rate.

12. The exercise system of claim 11, wherein the user interface permits the user to input physiological data permitting the system to automatically set a target heart rate.

13. A progressive heart rate monitor display for use with a heart rate monitor comprising:

a first indicia corresponding to a first heart rate; and
one or more additional indicia, each of the one or more additional indicia corresponding to a different heart rate, wherein the first indicia and the one or more additional indicia are consecutively positioned in a single array to provide an indication of a user's heart rate relative to a target heart rate, wherein one or more indicia corresponding with the target heart rate are actuated and one or more indicia corresponding with the user's heart rate are actuated when the user's heart rate is not the same as the target heart rate and only the one or more indicia representing the target heart rate are actuated when the user's heart rate is the same as the target heart rate.

14. The progressive heart rate monitor display of claim 13, further comprising a numeric display for representing the user's heart rate as a numeric value.

15. The progressive heart rate monitor display of claim 13, wherein the display is adapted to be utilized with an exercise apparatus.

16. The progressive heart rate monitor display of claim 13, wherein the progressive heart rate monitor display is configured to be worn by the user.

17. The progressive heart rate monitor display of claim 13, wherein the progressive heart rate monitor display is programmable.

18. The progressive heart rate monitor display of claim 17, wherein several different indicia are configured to represent the target heart rate and wherein a single indicia is selected based on the relationship of the user's heart rate to the target heart rate.

19. The progressive heart rate monitor display of claim 17, wherein a visual indication is provided to identify the indicia that represents the target heart rate.

20. The progressive heart rate monitor display of claim 19, wherein the indicia signal changes in the user's heart rate.

21. A method of displaying a user's heart rate relative to a target heart rate comprising:

providing a plurality of indicia adapted to identify a user's heart rate;
selecting a target heart rate, wherein one or more of the plurality of indicia comprise an indicator of a target heart rate;
monitoring the user's heart rate;
actuating one of the plurality of indicia as an indication of the user's heart rate; and actuating one or more of the plurality of indicia as an indication of the target heart rate, such that one or more of the plurality of indicia are actuated as an indication of the user's heart rate and in response to a change in the user's heart rate a different one or more indicia are actuated, wherein the one or more indicia representing the target heart rate are actuated in a manner so as to differentiate the target heart rate from the user's actual heart rate such that one or more of the plurality of indicia representing a range of heart rates below the target heart rate and the one or more indicia representing the target heart rate are actuated when the user's heart rate is the below the target heart rate, and one or more of a plurality of indivia above the target heart rate and the one or more indicia representing the target heart rate are actuated when the user's heart rate is above the target heart rate, and only the one or more indicia representing the target heart rate are actuated when the user's heart rate is the same as the target heart rate.

22. The method of claim 21, further comprising providing a display for representing the user's heart rate as a numeric value.

23. The method of claim 22, further comprising displaying the user's heart rate as a numeric value.

24. The method of claim 23, further comprising displaying the changed heart rate as a numeric value.

25. The method of claim 21, further comprising controlling operation of the exercise apparatus when the user's heart rate is above or below the target heart rate so that the user's heart rate approximates the target heart rate.

26. The method of claim 25, wherein controlling operation of the exercise apparatus comprises increasing the intensity of the workout program when the user's heart rate is below the target heart rate.

27. The method of claim 25, wherein controlling operation of the exercise apparatus comprises decreasing the intensity of the workout program when the user's heart rate is above the target heart rate.

28. The progressive heart rate monitor display of claim 21, wherein selecting a target heart rate is performed by a user.

29. The progressive heart rate monitor display of claim 28, wherein selecting a target heart rate is automatically performed.

30. A progressive heart rate monitor display configured to display a user's heart rate relative to a target heart rate, the progressive heart rate monitor display comprising:

a plurality of non-numeric indicia arranged in a single array, the non-numeric indicia corresponding to different heart rates, wherein at least one non-numeric indicia corresponding with the target heart rate is actuated and at least one non-numeric indicia corresponding with the user's heart rate is actuated when the user's heart rate is not the same as the target heart rate such that one or more of the indicia provide an indication of the user's heart rate relative to a target heart rate; and
a numeric display configured to represent the user's heart rate as a numeric value.

31. The progressive heart rate monitor display of claim 30, wherein the indicia comprise light emitting diodes.

32. The progressive heart rate monitor display of claim 30, wherein the indicia are colored to represent heart rates above, below, and approximating the target heart rate.

33. The progressive heart rate monitor display of claim 30, wherein the numeric display is configured to display two or more parameters relative to the user or workout routine.

34. The progressive heart rate monitor display of ciaim 33, wherein the numeric display alternatively displays the heart rate in beats per minute and the percentage of maximum recommended heart rate at which the user is exercising.

35. The progressive heart rate monitor display of claim 30, wherein the numeric display comprises a seven-segment display.

36. The progressive heart rate monitor display or claim 30, wherein the display comprises one of a plurality of screens between which a user can toggle.

37. The progressive heart rate monitor display of claim 30, wherein the progressive heart rate monitor display assists the user in selecting workout routines based on the physiological characteristics of the user.

* * * * *

UNITED STATES PATENT AND TRADEMARK OFFICE
CERTIFICATE OF CORRECTION

| | |
|---|---|
| PATENT NO. | : 7,097,588 B2 |
| APPLICATION NO. | : 10/367117 |
| DATED | : August 29, 2006 |
| INVENTOR(S) | : Watterson et al. |

Page 1 of 1

It is certified that error appears in the above-identified patent and that said Letters Patent is hereby corrected as shown below:

<u>Title Page</u>
Item 54, change "PROGRESIVE" to --PROGRESSIVE--
Item 57, Abstract, Line 5, change "users" to --user's--

<u>Column 1</u>
Line 1, Title, change "PROGRESIVE" to --PROGRESSIVE--

<u>Column 5</u>
Line 64, after "allowing" insert --the--

<u>Column 6</u>
Line 18, change "8" to --8a--

<u>Column 9</u>
Line 63, change "indivia" to --indicia--

Signed and Sealed this

Fifteenth Day of May, 2007

JON W. DUDAS
*Director of the United States Patent and Trademark Office*